United States Patent [19]
Brown

[11] Patent Number: 5,259,399
[45] Date of Patent: Nov. 9, 1993

[54] DEVICE AND METHOD OF CAUSING WEIGHT LOSS USING REMOVABLE VARIABLE VOLUME INTRAGASTRIC BLADDER

[76] Inventor: Alan Brown, 202 Twin Hills Rd., Longmeadow, Mass. 01106

[21] Appl. No.: 844,135

[22] Filed: Mar. 2, 1992

[51] Int. Cl.$^5$ .............................................. A61B 19/00
[52] U.S. Cl. ........................................ 128/897; 128/8
[58] Field of Search ............... 128/897–899, 128/8; 606/191, 192, 196, 198; 604/96–103, 54

[56] References Cited

U.S. PATENT DOCUMENTS

| | | |
|---|---|---|
| 4,133,315 | 1/1979 | Berman et al. |
| 4,246,893 | 1/1981 | Berson |
| 4,485,805 | 12/1984 | Foster, Jr. |
| 4,592,339 | 6/1986 | Kuzmak et al. |
| 4,648,383 | 3/1987 | Angelchik |
| 4,694,827 | 9/1987 | Weiner et al. |
| 4,723,547 | 2/1988 | Kullas et al. |
| 4,739,758 | 4/1988 | Lai et al. |
| 4,826,481 | 5/1989 | Sacks et al. |
| 4,899,747 | 2/1990 | Garren et al. |
| 5,084,061 | 1/1992 | Gau et al. |

FOREIGN PATENT DOCUMENTS 2822925  11/1979  Fed. Rep. of Germany ...... 128/899

OTHER PUBLICATIONS

Holt, Stephen et al., "Intragastric Devices for Weight Loss: Fact or Fancy?", The American Journal of Gastroenterology, vol. 83, No. 5, 1988, pp 554–555.
Schapiro, Melvin, M. D., "Has Bubble Therapy for Obesity Been Deflated?", Gastroenterology, vol. 95, No. 3, Sep. 1988, pp. 834–836.
The Gastric Bubble product literature of American Edwards Laboratories.

Primary Examiner—William E. Kamm
Assistant Examiner—J. P. Lacyk
Attorney, Agent, or Firm—Fish & Richardson

[57] ABSTRACT

A method and apparatus for causing weight loss in obese humans by occupying a segment of the stomach volume using a variable volume bladder filled with fluid. The bladder is inserted into the upper part of the stomach including the fundus through a percutaneous endoscopic gastrostony tube, which was non-surgically placed to create a permanent channel to the stomach. The inserted bladder is filled and emptied using a filling system for pumping fluid in and out of the bladder according to a predetermined scheme. The filling system comprises a reversible pump, a two-way valve connected to the filling tube, an electronic control means for automatically controlling the action of the filling system, and a battery. The electronic control means is connected to a plurality of sensors placed on the human body to detect digestion cycle and hemodynamic parameters. The electronic control means collects information detected by the sensors, governs the filling system according to the obtained information and predetermined operation scheme, and records times and volumes of the fluid transferred through the two-way valve.

15 Claims, 9 Drawing Sheets

DEVICE AND METHOD OF CAUSING WEIGHT LOSS USING REMOVABLE VARIABLE VOLUME INTRAGASTRIC BLADDER

BACKGROUND OF THE INVENTION

This invention relates to devices for medical treatment of morbid obesity in humans.

Morbid obesity is a chronic medical illness defined as overweight of 50 to 100 percent or 100 pounds above the ideal body weight.

Characteristic features of this illness include predominantly genetic origin, onset of disease in youth, a generally relentless progression throughout life, and a long-term cure rate of less than 5 percent. Morbid obesity has many serious health ramifications. A strong association exists between obesity and hypertension, hyperlipidemia and exacerbation of diabetes mellitus. These conditions, in turn, increase the risk factors for coronary artery disease (heart attack) and cardiovascular disease (stroke), which are leading causes of premature mortality and morbidity. Obesity also produces mechanical and physical stresses that aggravate or cause sciatica and joint problems, especially arthritis of the hips and knees. Another serious disease limited to obese individuals is a Pickwickian syndrome. This syndrome is characterized by nighttime episodes of upper airway obstruction which cause hypoxemia and, if left untreated, lead to pulmonary hypertension and heart failure. Weight loss will reverse this disease completely if instituted before permanent cardiac damage develops. Multiple other medical problems are more common in obese individuals such as gallstones, varicose veins, thromboembolism and hernias. In addition, morbid obesity can lead to psychosocial difficulties such as depression, loss of self-esteem and decreased employability.

To date, numerous attempts have been made to cause weight loss in morbidly obese patients. None of them have been entirely successful. The weight loss methods can be broadly divided into behavior modification and medical diets, surgical procedures, and devices.

Medical dietary regimes and behavior modification are used as a first line of treatment of obesity since they have almost no side effects or complications, when properly applied and monitored. However, these methods are usually unsuccessful in the treatment of morbid obesity because they depend solely upon the willpower of the patients. Only after these methods of treatment fail and the health risks of staying morbidly obese are judged to be serious, should interventional methods, including devices and surgical procedures, be employed. Behavior modification and medical diets, nevertheless, remain useful and necessary adjuncts to treatment by devices or surgery.

Surgical procedures for treatment of obesity include procedures that lead to weight loss by malabsorption such as jejunoileal or gastric bypass surgery, gastroplasty and gastric stapling and oral surgical procedures such as wiring shut the patient's jaws to reduce food intake. These procedures are usually quite effective in producing weight loss but some of them have been accompanied by serious complications and side effects, including operative mortality as high as three to six percent, postoperative wound infection, liver disfunction and failure, kidney stones, diarrhea and the need for further surgeries to treat intestinal obstruction or hernias, or to revise original surgery because of intolerable side effects.

Many weight loss devices are based on placing within the lumen of the stomach a bag or a balloon filled with air or liquid, which controls the patient's desire to eat by distension of the stomach. Theoretically, the distension of gastric by objects such as balloons as well as by food stimulates the neuroreceptors located in the submucosa of the upper fundus of the stomach, and these receptors send signals to the brain causing the patient to experience the sensation of satiety.

To date, two main approaches have been suggested to introduce inflatable balloon-like devices into the abdomen of obese patients. The first approach, suggested by Berson (U.S. Pat. No. 4,246,893), was surgical placement of the balloon-like device through an incision in the abdominal wall and the peritoneum into the upper abdomen adjacent and anterior to the stomach. The balloon is intended to exert pressure on the stomach from outside.

The second approach is placing the distensible device within the lumen of the stomach. This approach was described in the patent of Berman (U.S. Pat. No. 4,133,315), wherein an inflatable bag with a flexible tube is positioned in the stomach either non-surgically (i.e., through the mouth, down the esophagus and into the stomach), or surgically by creating a direct incision in the abdominal wall and performing a gastrostomy, with the filling tube surgically placed through the abdominal wall.

The surgical placement of the intragastric bag by performing a gastrostomy, as described by Berman, can be accompanied by serious complications and side effects associated with any surgical procedure and presents complications when the balloon needs to be replaced. In the case of having a filling tube permanently extended up through the esophagus and out of the nasal cavity or out of the mouth, as again described by Berman, is a major inconvenience for the patient. On the other hand, it is beneficial for the patient to fill and empty the intragastric balloon periodically. The emptying of the balloon provides periods of relief and feelings of well being for the patient.

The need for improvements over these approaches has been recognized for a number of years. Several proposals (Foster, Jr., U.S. Pat. No. 4,485,805; Lai et al., U.S. Pat. No. 4,739,758; Kullas et al., U.S. Pat. No. 4,723,547) use a free-floating balloon in the patient's stomach without having the filling tube attached. Since they recognized the importance of inflating and deflating the balloon and the above-discussed disadvantages of having a permanently attached filling tube, they constructed detachable means for filling or emptying the balloon introduced through the esophagus.

Similarly, Gan et al. (U.S. Pat. No. 5,084,061) recently proposed a free-floating inflatable intragastric balloon with a self-sealing valve, wherein the balloon is inflated or deflated using an endoscope introduced through the esophagus down to the stomach.

However, these proposals still have not allowed a frequent filling and emptying of the balloon on an hourly or daily basis since they require introduction of an endoscope through the esophagus, which is a procedure conducted by a physician on a sedated patient.

In summary, there continues to be a need for an intragastric device which can be nonsurgically placed in the lumen of the stomach and frequently filled and emptied, and in particular an intragastric device that is also easily withdrawn from the lumen of the stomach, inspected, replaced if needed, and reinserted into the lumen of the stomach. Preferably, all these steps should be done without any sedation or any major discomfort to the patient.

SUMMARY OF THE INVENTION

In one aspect of the invention, a method and system for use with the method is provided to cause weight loss in obese humans by occupying a segment of the stomach volume using a variable volume bladder, the bladder being positioned into and withdrawn from the stomach through a percutaneous endoscopic gastrostomy tube permanently placed to provide ready access to the lumen of the stomach through the thick abdominal wall. The method includes the steps of measuring the volume and location of the stomach including the fundus by radiological techniques, introducing the percutaneous endoscopic gastrostomy tube (P.E.G.) to establish access to the fundus of the stomach through the abdominal wall, selecting a bladder of size and shape to substantially occupy the upper part of the stomach including the fundus and the body of the stomach according to the performed radiological measurements, and inserting the bladder through the P.E.G. tube into the stomach so the size and shape of the bladder, cooperating with the position of placement of the P.E.G. tube, maintains the bladder in the upper part of the stomach including the fundus.

The method further includes the steps of filling and emptying the bladder repeatedly through a permanently connected filling tube that extends through the P.E.G. tube. The filled bladder occupies a large portion of the stomach to cause a feeling of satiety and to achieve decreased consumption of food by a patient. The emptying of the bladder provides periods of reduced trauma to the stomach.

Preferred embodiments of this aspect of the invention include introduction of the P.E.G. tube in the stomach of the obese person performed including the steps of inspecting the lumen of the stomach of the obese person using both an endoscope and a fluoroscope, wherein the endoscope is introduced into the stomach through the mouth down the esophagus, puncturing the abdominal wall with a needle, inserting a guidewire from outside through the puncture in the abdominal wall into the fundus of the stomach, and grasping the guidewire using the introduced endoscope and by pulling the endoscope out of the mouth extracting one end of the guidewire out of the mouth while the other end of the guidewire still remains outside of the abdomen. Subsequently, the P.E.G. tube is placed through the abdominal wall by performing the steps of attaching the tapered leading end of the P.E.G. tube to the guidewire extended out of the patient's mouth and pulling on the other end of the guidewire until the tapered end of the tube is pulled through the puncture opening in the abdominal wall, securing and sealing the placed gastrostomy tube on the stomach wall and on the abdominal wall, and cutting the P.E.G. tube to the appropriate length.

Preferred embodiments of this aspect of the invention may also include measuring the volume and location of the stomach employing an air contrast upper GI series by performing frontal and lateral projection radiographs or employing computerized tomography; removing the bladder from the gastric lumen through the P.E.G. tube as when it is desired to inspect or replace it; inserting an endoscope into the gastric lumen through the P.E.G. tube and examining the lumen for trauma or ulceration, and re-inserting through the P.E.G. tube a bladder into the stomach so that the size and shape of the bladder, cooperating with the position of placement of the P.E.G. tube, again maintains the bladder in the upper part of the stomach including the fundus and body of the stomach.

Preferred embodiments of this aspect of the invention may also include the feature of repeated filling and emptying of the bladder manually employing a filling system. The feature of repeated by filling and emptying the bladder automatically under control of an automatic filling system.

In another aspect of the invention, a medical device for treatment of morbidly obese patients comprising a bladder and a filling tube. The bladder is sized and shaped for occupying the upper part of the stomach. The bladder and the connectable filling tube are in collapsed condition before they are inserted through a P.E.G. tube into the stomach. The filling tube extends proximally through the P.E.G. tube for filling and emptying of the bladder.

Preferred embodiments of this aspect of the invention include a stylet extending into the bladder to enable thrusting of the collapsed bladder through the P.E.G. tube into the stomach.

In another aspect of the invention, a system for automatically filling and emptying a bladder positioned in the stomach is provided to cause weight loss in obese humans. The system is connected to the bladder through a filling tube and the system comprises a valve for controlling the amount of fluid introduced or evacuated from the bladder through the filling tube, a fluid reservoir for introducing fluid into the bladder through the valve, and electronic control means for controlling filling and emptying of the bladder according to a schedule or a set of selected conditions.

Preferred embodiments of this aspect of the invention include a plurality of sensors, connected to send information to the electronic control means, the sensors being placed in the human body to detect indicators of digestion and hemodynamic parameters in order to control the filling and emptying of the bladder.

Preferred embodiments of this aspect of the invention also include an electronic control means capable of keeping an electronic record of filling and emptying times and of the volume of fluid passed through the valve.

BRIEF DESCRIPTION OF THE DRAWINGS

FIGS. 2a-20c illustrate a method of introducing the P.E.G. tube.

DESCRIPTION OF THE PREFERRED EMBODIMENT(s)

Figure 1:
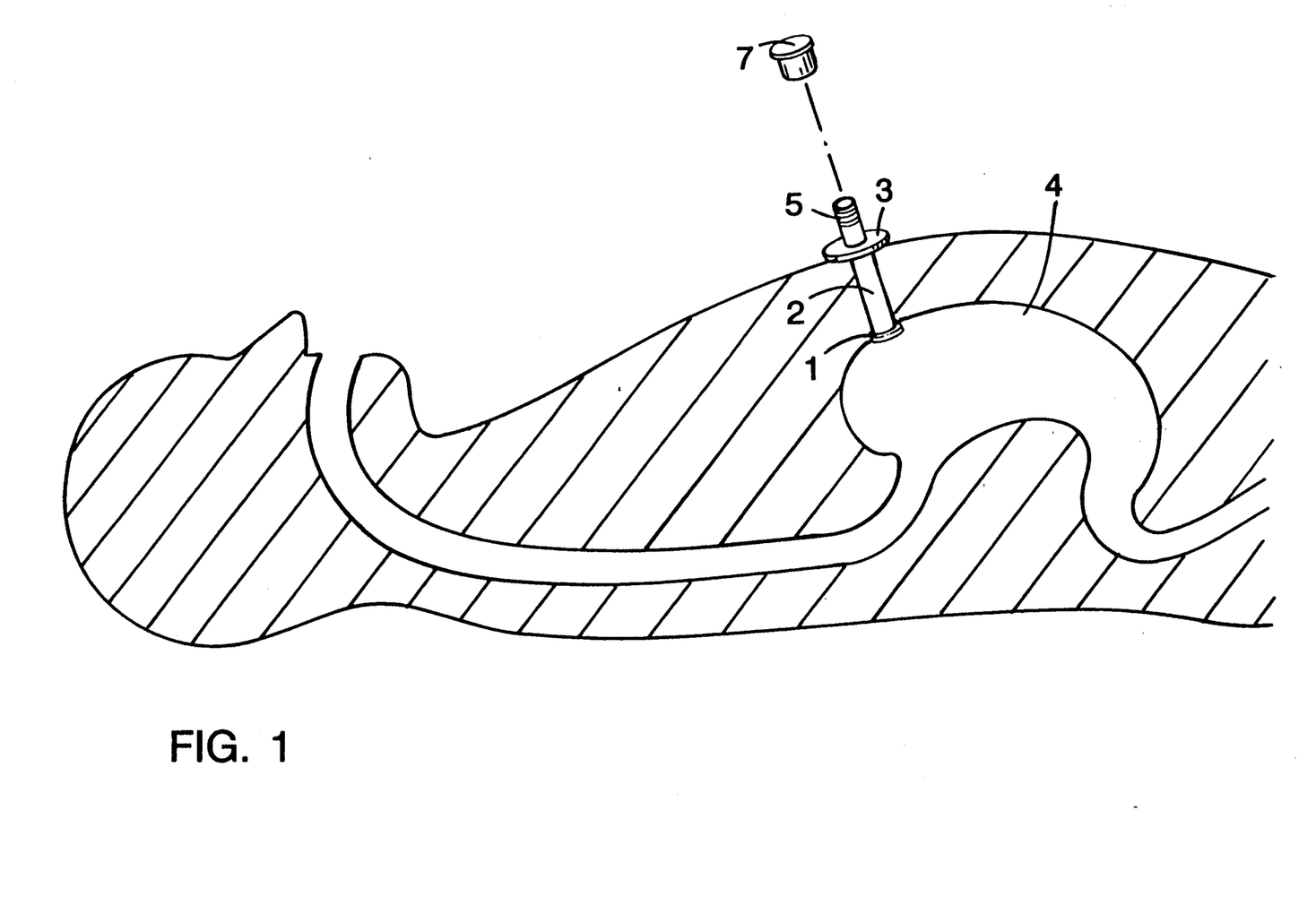
FIG. 1 shows a cross-sectional view of a patient lying in a supine position with a percutaneous endoscopic gastrostomy (P.E.G.) tube forming a channel across a thick abdominal wall of an morbidly obese person to the stomach.

Referring to FIG. 1, a morbidly obese patient, lying in a supine position on his back with his head to the left and his legs to the right, is shown in vertical longitudinal cross-section with a percutaneous endoscopic gastrostomy (P.E.G.) tube 2 in place. P.E.G. tube 2, creating a permanent channel to the stomach 4, is inserted into the fundus of the stomach by the Sacks-Vine method, or by the fastener method. The P.E.G. tube 2 has an outside diameter of about 26 to 30 French (about 8.3 to 9.5 millimeters) and its one end forms a locking means 1 which securely holds the P.E.G. tube 2 in the stomach. Locking means 1 is formed either by a flange, or by a balloon or by other configuration of protrusions preventing the tube to be pulled out of the stomach. The other end of P.E.G. tube 2 has an adapter 5 with outside threads 5 fitted to a plug 7. Plug 7, used when the weight-loss apparatus is not in place, can be threaded or friction set into adapter 5. A resilient skin disk 3 which tightly grips tube 2 is usually placed over P.E.G. tube 2; it secures P.E.G. tube 2 in place from outside against the abdominal wall.

Figure 2:
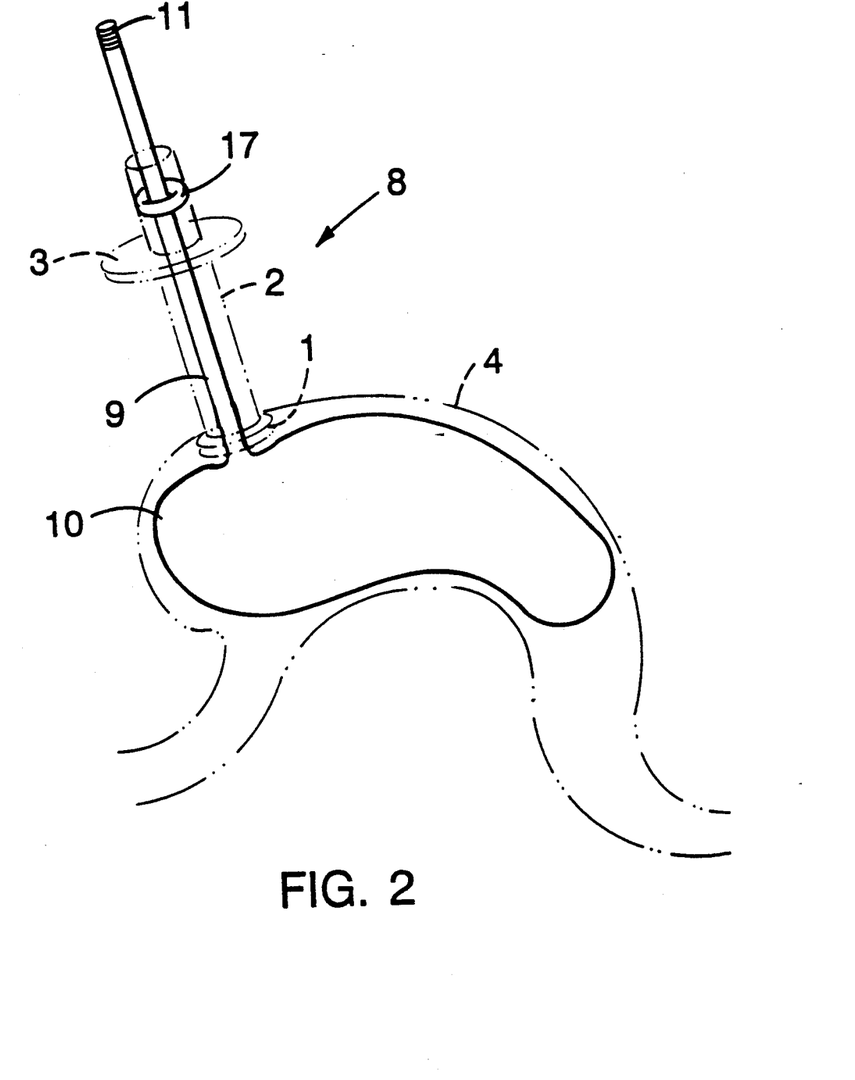
FIG. 2 shows the apparatus placed in the gastric lumen through the P.E.G. tube.
Figure 2A:
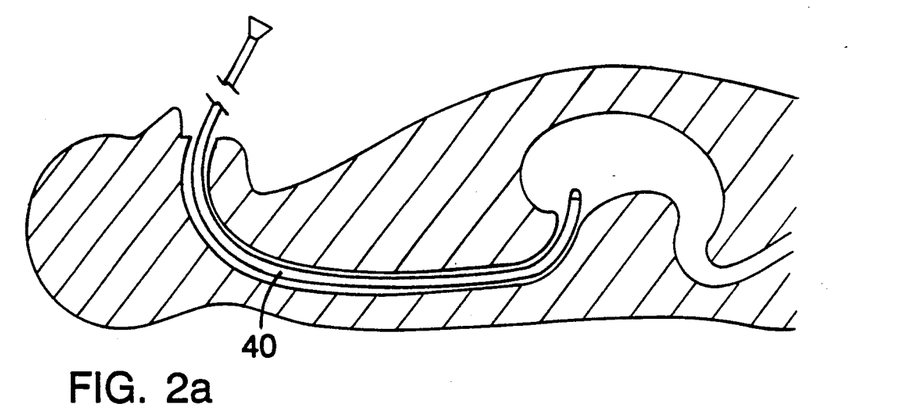
Figure 3:
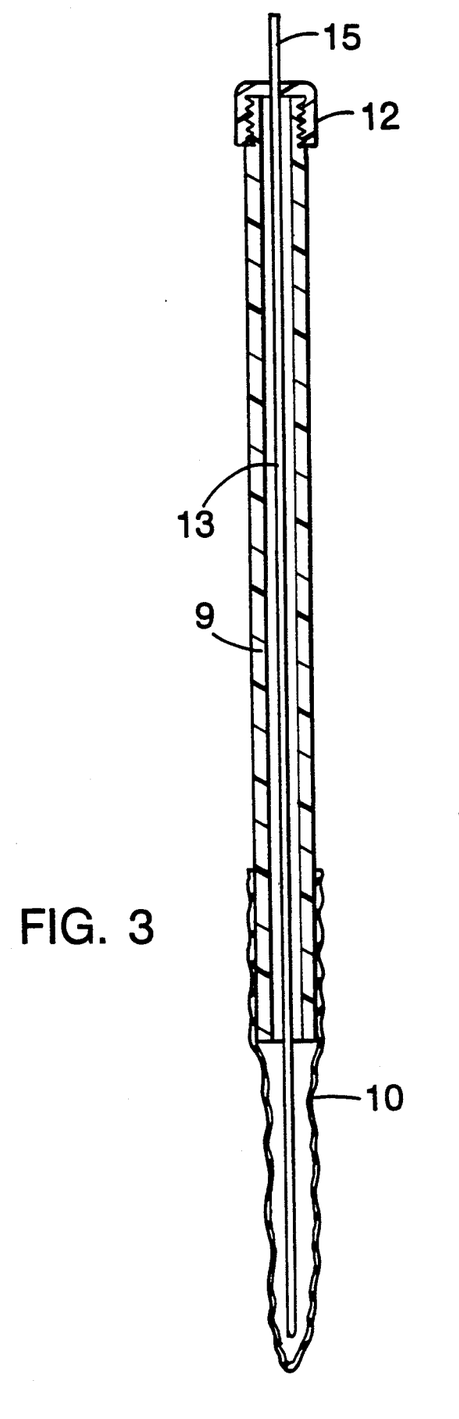
FIG. 3 shows a device comprising an inflatable bladder stretched by a stylet before insertion through the P.E.G. tube.
Figure 4:
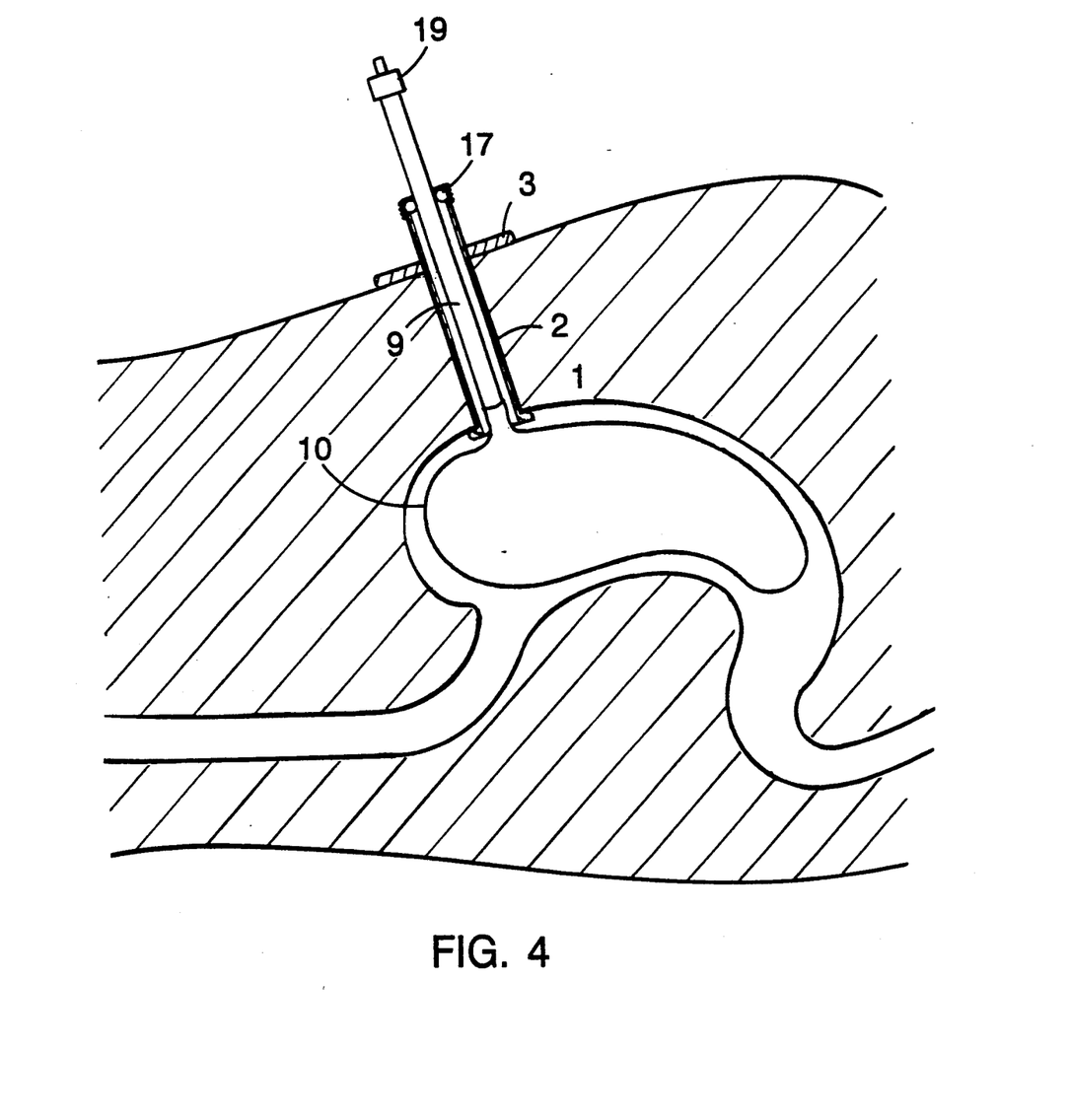
FIG. 4 shows the device positioned in the lumen of the stomach through the P.E.G. tube.

Referring to FIGS. 2 and 4, a weight-loss device 8 comprises a flexible filling tube 9, sized to pass through P.E.G. tube 2 connected to a selected bladder 10. Bladder 10 is a non-elastic bag made of a biocompatible material with a layer of radiopaque dye and is shaped to fit the stomach of this patient. The bladder has a volume of 1 to 2 liters and is envisioned to be selected from a set of sizes and shapes to custom fit to the size and shape of the particular patient's stomach. Filling tube 9 is much stiffer than bladder 10 so that it will retain its shape under pressure. Filling tube 9 is closely fitted to P.E.G. tube 2 without placing it under compression or disturbing it. Furthermore, filling tube 9 of P.E.G. tube 2 is fitted with several inches of a waterproof seal 17. Seal 17 prevents leakage of the stomach juices onto the patient's skin. The length of filling tube 9 is between 20 to 30 centimeters so that some excess length is attained. The portion of the filling tube extending from the P.E.G. tube is attached to the stomach wall. Outside, threads 11 of the free end of filling tube 9 are constructed to fit inside matching threads 14 of a screw-on stylet cap 12, as shown in FIG. 3. All parts used in construction of device 8 are made of durable and biocompatible material.

Referring to FIG. 4, P.E.G. tube 2 is introduced at a preselected point to ensure that access is gained to the upper part of the stomach called "fundus", in which it is desired to locate the bladder. In order to effectively control the patient's desire to eat, inflated bladder 10 is positioned primarily in the fundus where most of the neuroreceptors are located in the mucosa of the gastric wall. If pressure on the gastric wall is exerted, they send signals to the brain which cause satiety. Therefore it is critical to properly position bladder 10 in the stomach by selection of the point of percutaneous placement of the P.E.G. tube, as well as to select a bladder of an appropriate size. Thus, bladder 10 will primarily occupy the fundus and the upper part of the gastric lumen.

FIG. 3 illustrates a system and method for introducing the bladder 10 or device 8 into the stomach through P.E.G. tube 2. A hollow stylet 13 extends through a filling tube 9 into bladder 10 of apparatus 8. Hollow stylet 13 is longer than the device 8 so that a distal portion 13 extends beyond the filling tube and engages the far wall of the bladder. A proximal portion 15 also protrudes proximally from stylet cap 12. Vacuum is applied to extended portion 15 of hollow stylet 13 causing bladder 10 to collapse to the maximum degree i.e. vacuum compressed. The assembly 8 is then inserted through P.E.G. tube 2 into the stomach, the distal portion 13a of the stylet serving to stiffen the assembly so that it can be slid axially through the P.E.G. tube and into the stomach by thrust applied outside the abdomen. Once the bladder 10 reaches the stomach, air is introduced through hollow stylet 13 into bladder 10 and the inflated part of the bladder can help draw the rest of bladder 10 into the stomach.

Expansion of the gastric lumen by gas enables easy sliding of the apparatus 8 into the stomach. Bladder 10 is filled with fluid until it is fully extended in the lumen of the stomach. The position of bladder 10, which contains a layer of a radiopaque dye is confirmed using fluoroscopy.

The placement procedure includes measuring the size of the stomach and the location of the fundus and the pylorus of the stomach. On day 1 the patient comes to the radiology department and has an air contrast upper GI series taken after the patient has swallowed gas producing granules and radiology contrast fluid. The radiographs are taken in supine and erect position with a frontal projection and a lateral projection. The size and location of the stomach is thus determined from these radiographs. The computer tomography scanner can also be used; however, most of the morbidly obese patients will exceed the weight limit on the computer tomograph table. After the upper gastrointestinal series the patient is allowed to eat during day 1 including the evening meal. However, the patient is not allowed to eat thereafter.

Figure 2B:
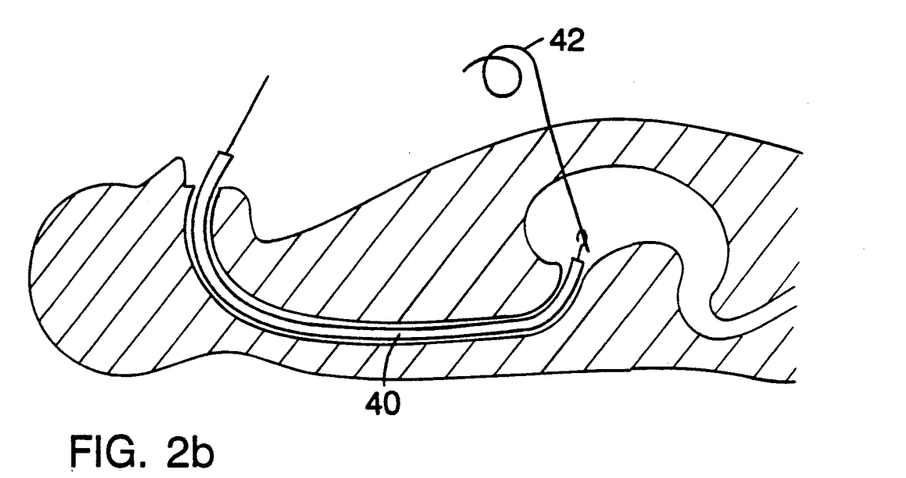
Figure 2C:
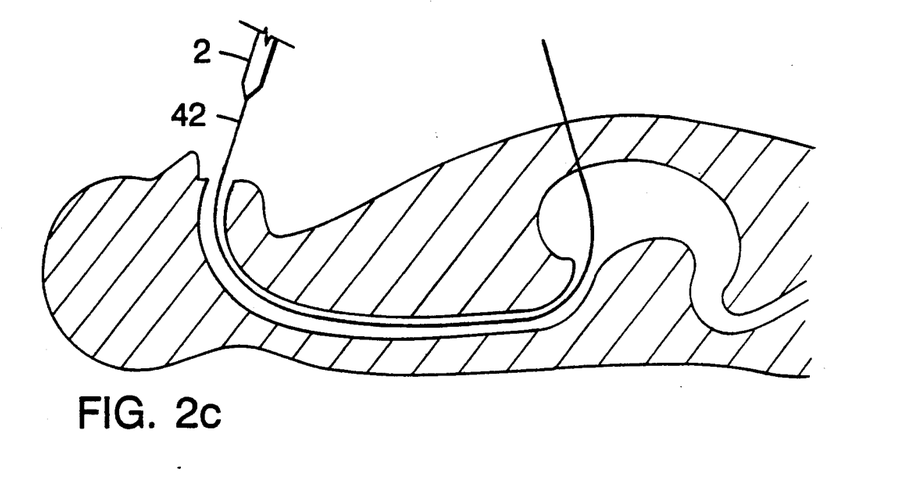
Figure 2D:
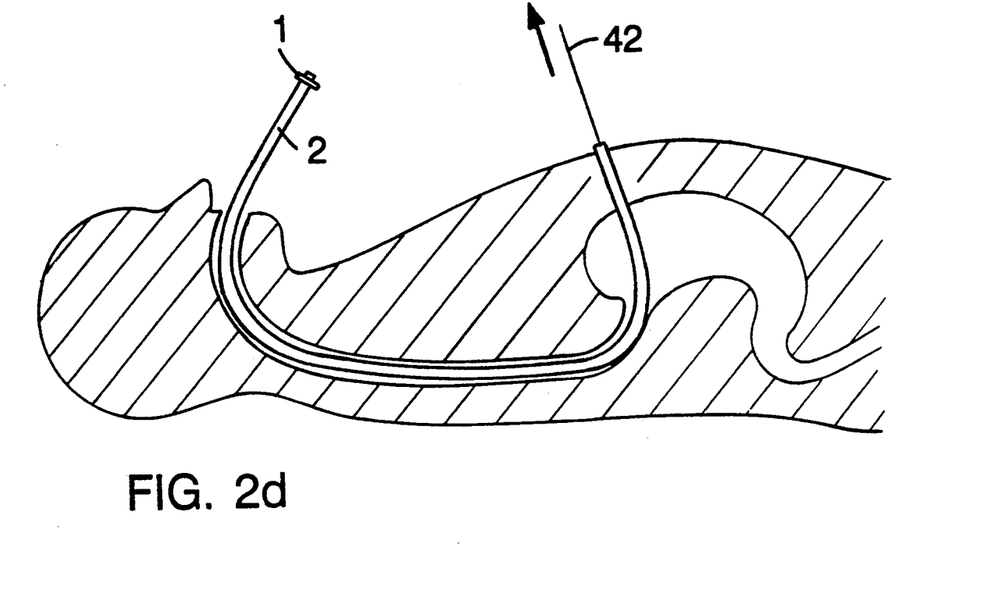
Figure 2E:
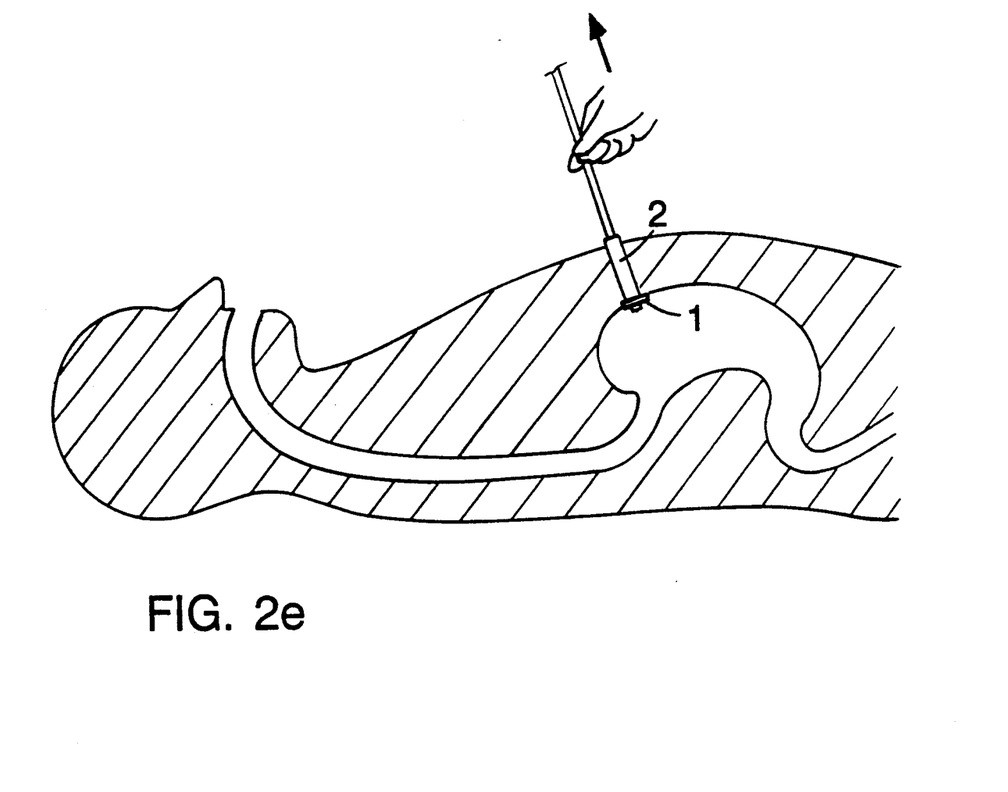
Figure 2F:
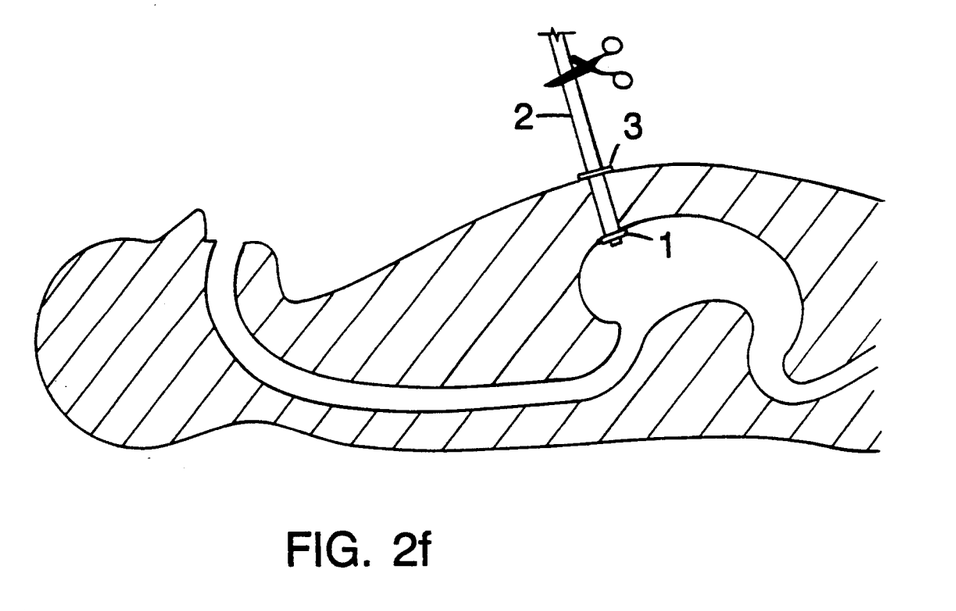

On day 2, by the morning the x-ray contrast has now progressed into the colon. Under the fluoroscope the colon is now clearly visible. Referring to FIGS. 2a-2f, an endoscope 40 is inserted down the esophagus in the usual way, and the stomach is inflated with air in order to examine the stomach walls. A proper location in the body of the stomach is chosen for insertion of the P.E.G. tube. That place is locally anesthetized. A tiny incision on the skin only is made and a needle is pushed through the abdominal wall from outside into the stomach while it is visualized by the endoscope, FIG. 2a. Through this needle a guidewire 42 is passed into the stomach. As shown in FIG. 2b, the guidewire is grasped by flexible forceps which are introduced through the endoscope's operating channel which is a part of the endoscope. The guidewire is then drawn up the esophagus and out of the mouth. The tapered end of P.E.G. 2 tube also called the Sacks-Vine tube is attached to the wire which protrudes out of the mouth. The narrow end of the P.E.G. tube with a loop at the end is attached to guidewire 42 shown in FIG. 2c. The wire with the attached tube is then drawn back through the esophagus into the stomach by pulling on the end of the wire protruding from the abdomen. As the guidewire is slowly pulled out, the tapered end of the P.E.G. tube enters and slowly increases the size of the puncture through the abdominal wall shown in FIG. 2d. The entire procedure is done only under local anesthesia. The tapered Sacks-Vine tube wedges through the layer of fat of the morbidly obese patient, typically six to eight inches. This process continues until flange 1 located at the end of the P.E.G. tube is tightly pressed against the stomach wall shown in FIG. 2e. Once a tight fit is achieved, the outside part of P.E.G. tube 2 is cut off to be the appropriate length. Skin disk 3 friction fed in place, and the P.E.G. tube is closed with a plug.

Seven to ten days later, the patient returns to have the pre-packaged and vacuum prepacked device 8, FIG. 3 inserted into the stomach. This time period is needed for proper healing of the abdominal wall, where the P.E.G. tube is inserted. The patient is asked to swallow gas producing granules in order to introduce air into the stomach. This opens a free space inside of the stomach, so that there is enough space for the bladder to be introduced and opened without any pressure against other organs. Accordingly, through the assistance of the distal end 13a of the distending stylet, the bladder 10 of the device is introduced into the stomach.

FIG. 4 shows the device 8 thus positioned in place. P.E.G. tube 2 has flange 1 which seals the gastric wall to prevent leakage of the gastric juices out of the gastric lumen. On the outside, friction skin disc 3 seals P.E.G. tube 2 against the abdomen and prevents the tube from falling into the stomach. A sealing O-ring 17 forms a water tight seal between P.E.G. tube 2 and filling tube 9 of apparatus 8 in order to prevent the gastric juices from leaking out onto the skin.

Figure 5:
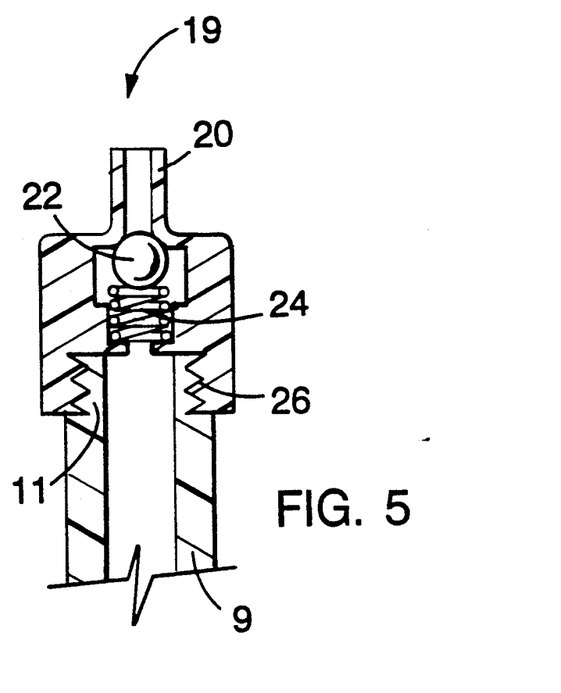
FIG. 5 shows a ball valve screwed on the filling tube of the apparatus.

Referring to the embodiment of FIG. 5, filling tube 9 is in this case sealed at the top by a ball valve 19. Ball valve 19 has an inlet passage 20, ball 22, a spring 24 and inside threads 26 which fit onto outside threads 11 of filling tube 9. The mechanism of the ball valve 19 prevents the bladder from emptying itself since the bladder is most of the time under positive pressure exerted by the abdomen. Ball valve 19 is designed to be used with a syringe to allow easy filling and emptying of bladder 10. If a tip of a syringe is introduced to inlet passage 20, ball 22 is pressed against spring 24; this enables filling or emptying of bladder 10 with gas or liquid.

Figure 6:
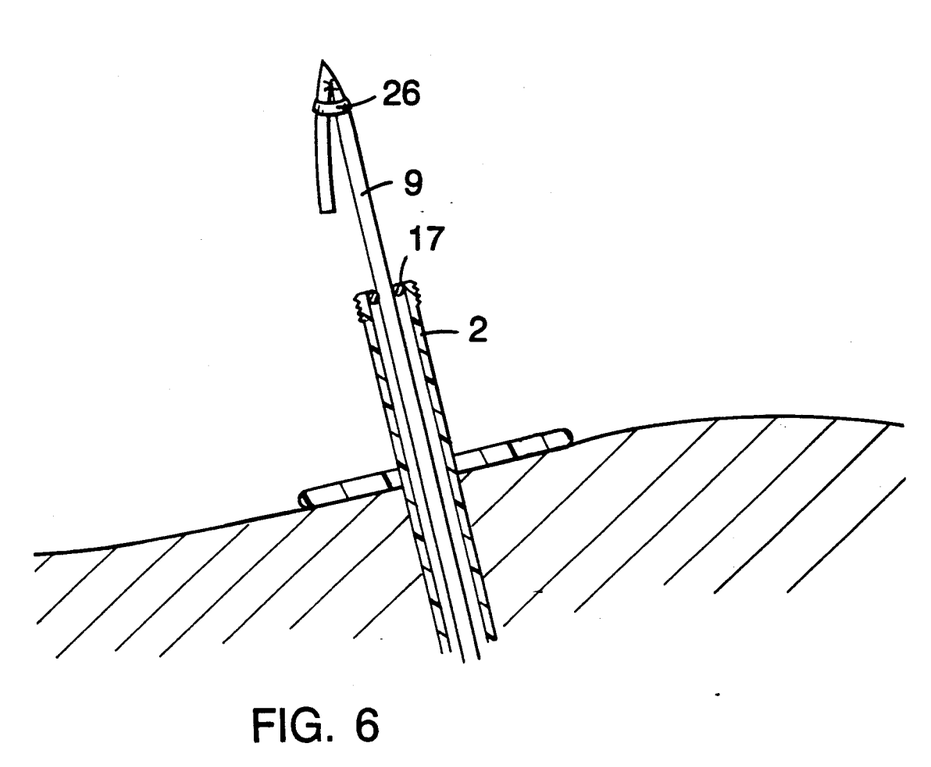
FIGS. 6 and 7 show a simple way of closing the filling tube on the apparatus inserted in the stomach through the P.E.G. tube.
Figure 7:
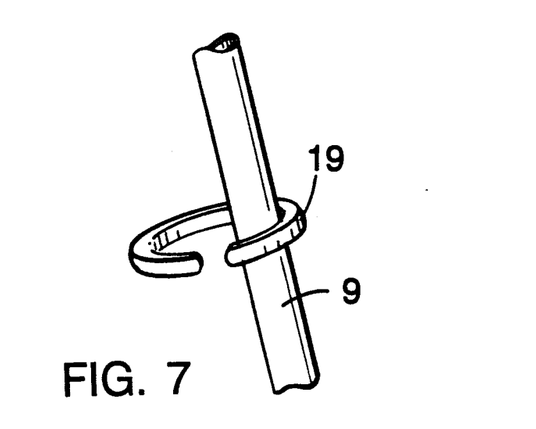

In another embodiment, filling tube 9 can be sealed by simply folding it, as shown in FIG. 6. To hold filling tube 9 folded, a clamp 26 is used. Clamp 26 can be replaced by a ring or rubber band. FIG. 7 shows ring 19 bonded to filling tube 9 used to close apparatus 8.

Figure 8:
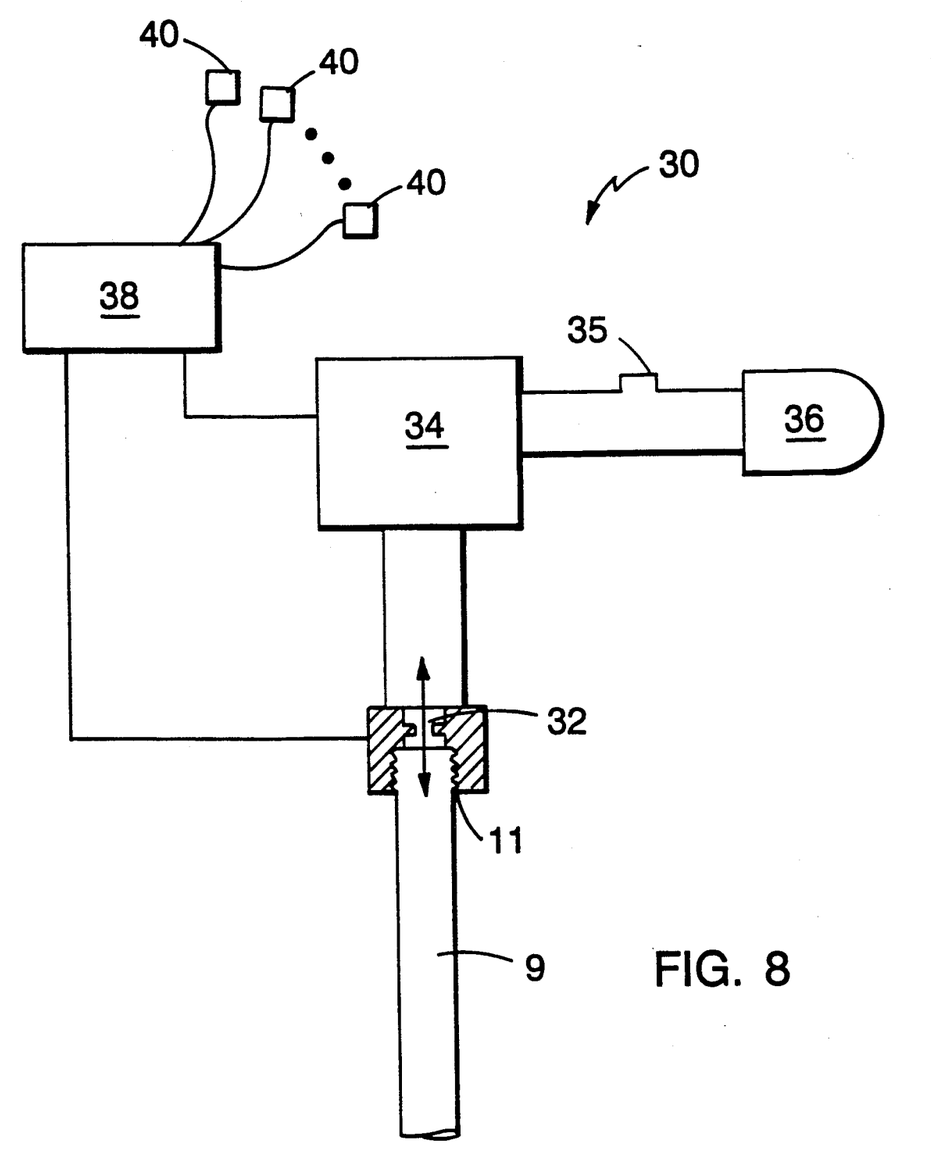
FIG. 8 shows a filling system designed to automatically fill and empty the bladder of the apparatus.

In another embodiment shown in FIG. 8, a filling system 30 automatically performs filling and emptying of the bladder. A two-way valve 32 of filling system 30 is attached to outside threads 11 of filling tube 9. Two-way valve 32 is connected to a pump 34 which forces fluid which advantageously may be liquid, in and out of the bladder into a fluid reservoir 36 according to a desired sequence. Operation of two-way valve 32 and pump 34 is automatically controlled by an electronic control means 38. Electronic control means 38 powered by a battery is connected to a plurality of sensors 40, which are placed on apparatus 8 and in several locations of the patient's body. The sensors monitor indicators of digestion and hemodynamic parameters of the patient. The sensors placed on bladder 10 in the gastric lumen can measure the acidity of the gastric juices, pressure on bladder 10 from outside exerted by the smooth muscle of the stomach and food present in the stomach. The sensors can further measure the body temperature, the pulse and other hemodynamic parameters. Filling system 30 is of hand-held size and weighs less than approximately 1 kg. Electronic control means 38 shares the information from the sensors and governs the filling and emptying process according to predetermined criteria. Two-way valve 32 is adapted to measure volume of fluid pumped through by pump 34. This information and the filling and emptying times are also recorded by electronic control means 38.

In another embodiment pump 34 is an air pump which forces air in and out of bladder 10. In this arrangement there is no fluid reservoir needed and an air port 35 is used. This pump may be actuated by the patient according to times or other criteria prescribed by the physician wherever the patient may be. In any event, a regime of frequent filling and emptying of the bladder is essential in order to prevent trauma to the gastric mucosa, which could be caused by permanently inflated bladder.

To remove apparatus 8 from the stomach of the patient one can simply withdraw the fluid from the bladder 10 through the stylet 13 by a syringe or using pump 34 and then pull the apparatus out of the stomach.

In another embodiment, bladder 10 is filled with a mixture of 80 to 90 percent of liquid such as water, or saline adding radiopaque contrast fluid and 10 to 20 percent of air. This mixture of liquid and air will tend to keep the filled bladder 10 floating on top of the solid and liquid food in the upper anterior part of the stomach and away from the pylorus, thus making an gastric outlet obstruction by bladder 8 less likely.

What is claimed is:

1. A method of causing weight loss in obese humans by occupying a segment of the stomach volume using an inflated bladder, said method comprising the steps of:
   (a) measuring the volume and location of the stomach including the fundus by radiological techniques,
   (b) selecting a bladder contoured in size and shape to substantially occupy the fundus or the body of the stomach measurement,
   (c) introducing by percutaneous endscopic techniques a percutaneous endoscopic gastrostomy (P.E.G.) tube to establish access from the outside to the body of the stomach through the abdominal wall,
   (d) inserting said bladder through said percutaneous endoscopic gastrostomy tube into the stomach so the size and shape of said bladder, cooperating with the position of placement of said gastrostomy tube, maintains said bladder in the upper part of the stomach including the fundus, and
   (e) filling and emptying said bladder with fluid repeatedly over time through a filling tube that extends through said gastrostomy tube, in the manner that said bladder when filled occupies a large portion of said stomach to cause a feeling of satiety, thereby to achieve decreased consumption of food by a patient, and said emptying of said bladder provides periods of reduced trauma to the stomach to promote the patient's health and feeling of well being, said bladder capable of being withdrawn from said stomach through said P.E. G. tube to enable inspection and replacement and to enable ready access to the lumen of the stomach through the abdominal wall.

2. The method of claim 1 wherein said measurement of the volume and location of said stomach is conducted by employing an air contrast upper GI series, including the making of frontal and lateral projection radiographs.

3. The method of claim 1 wherein said measurement of the volume and location of said stomach is conducted by employing computerized tomography.

4. The method of claim 1 wherein said introduction of said P.E.G. tube in said obese person comprises the steps of:
   (a) inspecting said stomach of said obese person using both an endoscope and a fluoroscope, said endoscope introduced into the stomach through the mouth down through the esophagus,
   (b) establishing a location for said gastrostomy tube placed to maintain said bladder in the desired position,
   (c) when a needle, forming a puncture in the abdomen at said location, the needle passing through the thick layer of abdominal fat of said obese person, and via said puncture inserting a guidewire from outside through the abdominal wall into said fundus of said stomach, grasping the distal portion of said guidewire using said introduced endoscope and by pulling said endoscope out of the mouth extracting the distal end of said guidewire out of the mouth while the proximal end of said guidewire is held outside of the puncture formed in the abdomen,
   (d) placing said gastrostomy tube through the abdominal wall by attaching said gastrostomy tube to the distal portion of said guidewire while said portion extends out of the patient's mouth and pulling on the proximal end of said guidewire until said percutaneous endoscopic gastrostomy tube passes through the esophagus, stomach, and abdominal wall to the outside, and
   (e) securing said sealing said placed gastrostomy tube on the stomach wall and on the abdominal wall and cutting said gastrostomy tube to the appropriate length.

5. The method of claim 1 further comprising the steps of:
   (a) removing said bladder from the stomach through said gastrostomy tube,
   (b) inserting an endoscope into the stomach through said gastrostomy tube in order to examine the gastric wall for trauma and ulceration, and
   (c) re-inserting said bladder through said gastrostomy tube into the stomach so the size and shape of said bladder, cooperating with the position of placement of said gastrostomy tube, again maintains said bladder in the fundus or the body of the stomach.

6. The method of claim 1 wherein said repeated filling or emptying said bladder is automatically controlled by a filling system.

7. The method of claim 1 further including the steps of:
   (a) detecting condition of said obese patient with sensors measuring indicators of digestion and hemodynamic parameters,
   (b) transmitting information from said sensors to an electronic control means linked to a filling system used for filling and emptying said bladder, and
   (c) controlling filling and emptying of said bladder by said filling system using said electronic control means.

8. The method of claim 6 wherein said filling and emptying of said bladder being performed by a reversible air pump forcing air into said bladder or releasing air from said bladder as governed by said electronics control means receiving input from said sensors and operating according a predetermined procedure.

9. The method of claim 6 further including manually inducing said filling or emptying of said bladder by overriding said electronics control means connected to said filling system.

10. A medical device for treatment of obese humans by occupying a segment of the stomach volume comprising
    a bladder sized and shaped to substantially occupy the fundus or the body of the stomach,
    a filling tube connectable to said bladder for repeated filling and emptying of said bladder located in the stomach of said obese humans, and
    said filling tube and said bladder collapsed in condition to pass through a percutaneous endoscopic gastrostomy (P.E.G.) tube into the stomach, said filling tube having sufficient lengths to extend proximally through said gastrostomy tube to enable said filling and emptying of said bladder.

11. The device of claim 10 including a stylet extending into the bladder to enable thrusting of the collapsed bladder through said P.E.G. tube into the stomach.

12. A system for automatically filling and emptying a bladder positioned in the stomach to enable weight loss in obese humans, said system being connected to a bladder through a filling tube, said system comprising
    (a) a valve adapted to control amount of fluid introduced or released from said bladder through said filling tube,
    (b) a reservoir of fluid for introduction into said bladder through said valve, and
    (c) an electronics control means for controlling filling and emptying said bladder with said fluid according to a predetermined set of criteria.

13. A system for automatically filling and emptying a bladder positioned in the stomach in order to cause weight loss in obese humans, said system being connected to said bladder through a filling tube, said system comprising
    (a) a valve for controlling amount of fluid introduced or released from said bladder through said filling tube,
    (b) a pump for introducing air into said bladder through said valve, and
    (c) an electronics control means for controlling filling and emptying said bladder with said fluid according to a predetermined set of criteria.

14. The system of claim 12 or 13 further comprising a plurality of sensors connected to provide information to said electronic control means,
    said sensors being placed in the human body to monitor indicators of digestion or hemodynamic parameters and said electronic control means adapted to control said filling and emptying of said bladder in accordance with digestive cycles corresponding to said indicators.

15. A system of claim 12 or 13 wherein said electronic control means is adapted to keep an electronic record of inflation and deflation times and volumes of fluid passed through said valve.

* * * * *